(12) United States Patent
Trudsoe et al.

(10) Patent No.: US 8,895,513 B2
(45) Date of Patent: Nov. 25, 2014

(54) PERSONAL CARE COMPOSITIONS WITH ACIDIFIED PECTINS

(71) Applicant: CP Kelco ApS, Lille Skensved (DK)

(72) Inventors: Jens Eskil Trudsoe, Roskilde (DK); Helle Bech Olsen, Haslev (DK)

(73) Assignee: CP Kelco ApS (DK)

( * ) Notice: Subject to any disclaimer, the term of this patent is extended or adjusted under 35 U.S.C. 154(b) by 0 days.

(21) Appl. No.: 14/145,382

(22) Filed: Dec. 31, 2013

(65) Prior Publication Data

US 2014/0120044 A1 May 1, 2014

Related U.S. Application Data

(62) Division of application No. 13/410,540, filed on Mar. 2, 2012, now Pat. No. 8,685,420.

(51) Int. Cl.
| | |
|---|---|
| A61K 38/00 | (2006.01) |
| A61K 8/73 | (2006.01) |
| A61Q 19/00 | (2006.01) |
| A61K 8/04 | (2006.01) |
| A61Q 15/00 | (2006.01) |
| A61Q 19/04 | (2006.01) |
| A61Q 19/10 | (2006.01) |
| C11B 9/00 | (2006.01) |

(52) U.S. Cl.
CPC . *A61K 8/73* (2013.01); *A61Q 19/00* (2013.01); *A61K 8/042* (2013.01); *A61Q 15/00* (2013.01); *A61Q 19/04* (2013.01); *A61Q 19/10* (2013.01); *C11B 9/00* (2013.01)
USPC .......................................... 514/18.6; 424/401

(58) Field of Classification Search
None
See application file for complete search history.

(56) References Cited

U.S. PATENT DOCUMENTS

| | | | |
|---|---|---|---|
| 2,480,710 A | 8/1949 | Bryant | |
| 7,799,356 B2 | 9/2010 | Raschke et al. | |
| 2006/0127991 A1 | 6/2006 | Christensen et al. | |
| 2007/0092622 A1 | 4/2007 | Trudsoe | |
| 2007/0160734 A1 | 7/2007 | Van Bokkelen | |
| 2008/0306020 A1 | 12/2008 | Trudsoe | |

(Continued)

FOREIGN PATENT DOCUMENTS

| | | |
|---|---|---|
| EP | 664300 B1 | 4/2004 |
| EP | 1294773 B1 | 8/2006 |

(Continued)

OTHER PUBLICATIONS

Siti Nurdjanah, Extraction and Characterization of Pectin from Australian and Indonesian Sweet Potato (*Ipomoea batatas* L.), A Thesis submitted to The University of New South Wales, Feb. 2008.

(Continued)

*Primary Examiner* — Anand Desai
*Assistant Examiner* — Melissa Mercier
(74) *Attorney, Agent, or Firm* — Sutherland Asbill & Brennan LLP

(57) ABSTRACT

Personal care compositions are provided that include acidified pectins at a concentration of about 2 to about 5% by weight. The acidified pectin includes a low ester pectin with a degree of esterification of about 30 to about 50 and a pH of about 2 to about 4. Desirably, the personal care composition is characterized as a viscous, fluid gel. Also provided are methods for preparing personal care compositions and methods for the use of personal care formulations.

20 Claims, 1 Drawing Sheet

(56) References Cited

U.S. PATENT DOCUMENTS

| | | |
|---|---|---|
| 2010/0247582 A1* | 9/2010 | Sorensen et al. .............. 424/400 |
| 2011/0206811 A1 | 8/2011 | Sarig et al. |
| 2011/0224167 A1 | 9/2011 | Trudsoe |

FOREIGN PATENT DOCUMENTS

| | | | |
|---|---|---|---|
| EP | 2081446 | B1 | 1/2011 |
| WO | 2007050711 | A2 | 5/2007 |
| WO | 20100037636 | A2 | 4/2010 |
| WO | 2010129153 | A2 | 11/2010 |

OTHER PUBLICATIONS

PCT/EP2013/052480 International Search Report and Written Opinion dated Jan. 30, 2014.

* cited by examiner

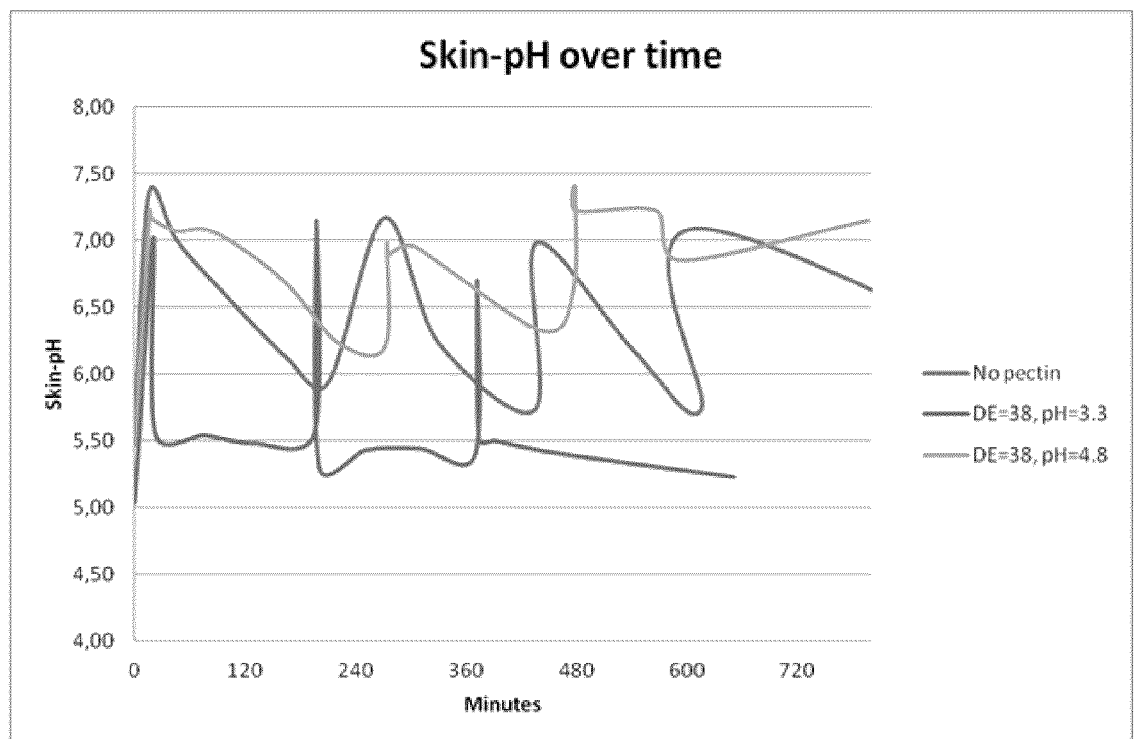

PERSONAL CARE COMPOSITIONS WITH ACIDIFIED PECTINS

CROSS-REFERENCE TO RELATED APPLICATIONS

The present application is a divisional of U.S. application Ser. No. 13/410,540, filed Mar. 2, 2012, now pending. This application is incorporated herein by reference in its entirety.

TECHNICAL FIELD

Embodiments of the present description relate to acidified pectins and their use in personal care compositions. In particular, the present description relates to personal care compositions characterized as being viscous, free-flowing solutions with gel-like properties prepared with acidified low ester pectins.

BACKGROUND

The mammalian epidermis serves many functions, amongst which are formation and maintenance of a cohesive permeability barrier that guards against excessive transcutaneous water loss and as an external barrier against microbial attack. The outermost layer of the epidermis, the stratum corneum, has a strongly acidic pH, with the pH of the upper stratum corneum being approximately 4.5-5.0 and the pH of the lower stratum corneum approaching neutral. Thus, the stratum corneum experiences a pH differential of more that two pH units over a vertical space of less than 100 microns; a dramatic biological phenomenon. This pH gradient occurs not only in human skin, but also in rodent skin despite its much thinner stratum corneum.

Although first recognized decades ago, an understanding of the origin and function of the buffering capacity of the stratum corneum, often referred to as the "acid mantle", is incomplete. Whatever the nature of its origin, however, it is known that the acid mantle is essential to normal functioning of the stratum corneum. For example, the acidic pH of the human skin assists in both the regulation of the cohesion of the stratum corneum as well as its barrier function.

The acidic pH of the acid mantle also appears to be necessary for maintaining the lipid barrier, which makes the skin impenetrable to bacteria. The pH of healthy skin naturally increases and recovers, but recovery slows as people age. At higher pHs, around neutral or basic, the lipid barrier deteriorates and the repair process is inhibited. For example, the hydrolase enzyme, Beta-glucocerebrosidase, assists in the post secretory processing of polar lipid precursors into non-polar lipid products within the stratum corneum interstices. The optimum pH of Beta-glucocerebrosidase is approximately 5.5; however, its activity is inhibited at a lower pH of 3.5-4, and is absent or significantly reduced at a neutral pH. Thus, in developing skin care products a particularly desirable effect would be to both reduce the stratum corneum pH as fast as possible to a pH of about 5.5 (i.e., the optimum pH of Beta-glucocerebrosidase) and maintain the pH at that level.

Most skin care products are neutral or slightly alkaline and are relatively stable toward pH changes after topical application. Unfortunately, a neutral or alkaline pH is not favorable for repair of the stratum corneum lipid barrier. Acidic skin care products with a pH matching that of the acid mantle have also been used for treating the skin. Typically, these products use ordinary acids, such as citric acid, hydrochloric acid or retinoic acid, at concentrations of less than 0.1 weight percent which reduces the pH of the product but does not provide buffering effect to lower the pH of the acid mantle. If added at higher concentrations, the ordinary acids can harm the skin, are highly irritating, and often result in peeling of the skin.

Alternatively, low ester pectin has been used as an acidic material for providing buffering effect without harm to the skin. Since low ester pectin being a polymeric material has significantly higher molecular weight than ordinary acids, pectin does not penetrate and harm the skin as does the ordinary acids. However, pectin presents some difficulties in use with respect to its rheological properties and its limiting ability to provide buffering effect due to low ester pectin having a pH of about 4.

The rheological properties of the compositions, which affect the visual appeal and desired flowability and spreadability during use, are an equally important feature in skin care products. For example, thick, non-tacky and non-astringent skin care formulations are often made with polyacrylate, which have a molecular weight on the order of 100,000 and provide the desired rheological properties. When made with natural polysaccharides (e.g., carrageenan or xanthan gum), however, the skin care formulations become tacky and astringent. Without being bound of theory, it is believed that the molecular weight of many natural polysaccharides (e.g., carrageenan or xanthan gum) is at least in part responsible for the tackiness and the astringency that are observed—i.e., carrageenan and xanthan gum have molecular weights on the order of 1 million and 10 million, respectively, as compared to the significantly lower molecular weight of polyacrylates.

Although pectin has a molecular weight comparable to polyacrylates and can provide the desired buffering effect, pectin without the use of other rheological imparting ingredients lacks any texture and is liquid. Prior art compositions including pectin generally contain 1.5 weight percent or less of pectin and rely on the use of other ingredients to impart the desired texture and rheology to the compositions. Commonly used texture-modifying ingredients include emulsifiers; however, the emulsifiers also will emulsify the skin fat. Low ester pectin having a degree of esterification in the range of 5 to 10 has been used in skin care formulations for its buffering effects. However, such pectin products are unable to provide texture to the preparation, which means that other ingredients are necessary to provide the desired texture.

Thus, there remains a need to develop a personal care composition that has desirable textural and rheological properties without requiring use of polyacrylates, emulsifiers, and low molecular weight acids that may irritate the skin.

SUMMARY

Embodiments of the present application addresses the above-described needs by providing personal care compositions comprising an acidified pectin at a concentration of about 2 to about 5% by weight. The acidified pectin comprises a low ester pectin with a degree of esterification of about 30 to about 50 and a pH of about 2 to about 4. Desirably, the personal care composition is characterized as a viscous, fluid gel.

In another aspect, embodiments of the present description include methods for preparing personal care compositions having the desired textural and rheological properties. The method may comprise mixing an acidified pectin with demineralized water to provide a mixture of a personal care composition, heating the mixture to a temperature of about 70 to about 90° C. for a time sufficient to dissolve the acidified pectin in the personal care composition, and cooling the personal care composition to a temperature below about 70° C.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 1 is a graph comparing the effect of personal care formulations having various pectins on the skin pH.

DESCRIPTION

Embodiments of the present description include personal care compositions comprising acidified low ester pectins, methods for their formulation, and use. Desirably, the acidified low ester pectin is present in the personal care composition at a concentration of about 2 to about 5% by weight and the personal care composition is characterized as a viscous, free-flowing solution having gel-like properties.

As used herein, the phrases "gel-like", "liquid gel", and "fluid gel" are synonymous, and generally describe a composition having properties of both liquids and gels (i.e., are characterized at the macroscopic level as a liquid and the microscopic level as a dispersion of small broken bits of gel). Fluid gel compositions can be distinguished from self-supporting gels, which typically are thick or viscous to the point that they are not readily pourable. Fluid gel compositions also are distinct from liquids, which typically lack any texture. For example, a fluid gel composition can be squeezed out of a tube while maintaining its homogeneity or can be picked-up in small portions and spread on the skin without showing lumps. Thus, fluid gel compositions range in viscosity from being pourable to spreadable.

Acidified Low Ester Pectins

As used herein, the phrases "acidified low ester pectin" and "acidified pectin" are used interchangeably to describe pectins having a degree of esterification (DE) of about 30% to about 50% and a pH of about 2 to about 4. In embodiments, the acidified low ester pectins have a DE in the range of about 30% to about 40% and a pH in the range of about 2.5 to about 3.7. For example, in an embodiment the acidified low ester pectin has a DE of about 30% to about 35% and a pH of about 2.9 to about 3.7, or more particularly from about 3.4 to about 3.6. In another embodiment the acidified low ester pectin has a DE of about 36% to about 50% and a pH of about 2.8 to about 3.6.

Pectins are complex polysaccharides associated with plant cell walls. It consists of an alpha 1-4 linked polygalacturonic acid backbone intervened by rhamnose residues and modified with neutral sugar side chains and non-sugar components such as acetyl, methyl, and ferulic acid groups. The pectins may be extracted from pectin-containing plant materials using methods known to those skilled in the art. The extracted pectins then may be de-esterified to obtain a low ester pectin having the desired DE. Generally, such low ester pectins have a pH of about 4 to about 5. The de-esterified low ester pectins then can be subsequently acidified.

In embodiments, the low ester pectins are acidified by mixing the low ester pectin with a solution of an acid and alcohol for a time sufficient to obtain an acidified pectin having the desired pH, washing the acidified pectin with an alcohol, and drying the acidified pectin. Any number of desired washing steps may be used to remove excess acid from the acidified pectin. In embodiments, the alcohol may be a primary or a secondary alcohol and the acid may be an organic acid or a mineral acid. Non-limiting examples of primary or secondary alcohols suitable for use in embodiments include ethanol, methanol, and iso-propanol. Non-limiting examples of acids suitable for use in embodiments include hydrochloric acid, sulfuric acid, sulfuric acid, nitric acid, and phosphoric acid.

Personal Care Compositions

The acidified pectins provided herein are particularly effective for use in personal care compositions and desirably are in a form suitable for use on mammalian skin, or more particularly, on human skin.

"Personal care composition" as used herein, refers to compositions intended for topical application to the skin or hair, non-limiting examples of which include a styling gel, a moisturizer, a lotion, a deodorant, a toothpaste, a body wash, a bath gel, a body gel, a hand sanitizer, a shampoo, a conditioner, or combinations thereof.

Those skilled in the art will appreciate that the rheological properties of the personal care products may be modified, in part, by modifying the amount of the acidified low ester pectin present in the personal care product. In one embodiment, the acidified low ester pectin is present in the personal care product in an amount from about 2.0% to about 4.0% by weight of the personal care product. For example, in embodiments the acidified low ester pectin may be present in the personal care product in an amount from about 2.5% to about 4.0% by weight, in an amount from about 2.5% to about 3.5% by weight, in an amount from about 3.0% to about 4.0% by weight, or in an amount from about 2.5% to about 3.0% by weight.

The personal care products of the present description may further comprise one or more additional components known for use in personal care products, provided that the additional components are physically and chemically compatible with the acidified low ester pectins provided herein, or do not otherwise unduly impair product stability, aesthetics, or performance. Individual amounts of such additional components may range from about 0.001% to about 95% by weight of the personal care product. The additional components may be water soluble (i.e., soluble in water at 25° C.) or water insoluble (not soluble in water at 25° C.).

Non-limiting examples of such additional components that may be suitable for use in embodiments of the personal care compositions include conditioning agents, silicones, hydrocarbon oils, fatty esters, particles, suspending agents, paraffinic hydrocarbons, propellants, viscosity modifiers, dyes, non-volatile solvents or diluents, pearlescent aids, foam boosters, ionic and nonionic surfactants, ionic and non-ionic co-surfactants, pH adjusting agents, perfumes, preservatives, chelating agents, pediculides, proteins, skin active ingredients, sunscreens, UV absorbers, vitamins, fatty acids, and fatty oils.

Although the personal care compositions may include additional components, embodiments of the personal care compositions provided herein desirably are substantially free of low molecular weight acids and/or emulsifiers, which commonly are used to impart the desired textural and rheological properties to the personal care compositions. As used herein, the phrase "substantially free" means that an insignificant amount of the component is present in or purposefully added to the composition. Accordingly in certain embodiments the personal care compositions consist essentially of the acidified low ester pectins.

The personal care compositions provided herein desirably are characterized as having a gel-like texture, being non-tacky to tacky on the skin, and non-astringent. As used herein, the term "tacky" describes a composition that is slightly adhesive or gummy to the touch, and may be characterized as being sticky. As used herein, the term "astringent" describes a composition that shrinks or constricts body tissue. Thus a "non-tacky" or "non-astringent" composition is one that is not "tacky" or is not "astringent". These features often may be characterized as least in part by the viscosity of the compositions, which in embodiments may be in the range of about 30,000 cP to about 400,000 cP. For example, in embodiments an acidified low ester pectin with a DE of 30% and a pH of 2.9 to 3.7 at a concentration in the range of 2% to 4% imparts a viscosity to a personal care composition of about 75,000 cP to about 400,000 cP. In another embodiment, an acidified low ester pectin with a DE of 38% and a pH of 2.8 to 3.6 at a concentration in the range of 3% to 4% imparts a viscosity to a personal care composition of about 30,000 cP to about 40,000 cP.

Methods of Manufacturing Personal Care Compositions

In another aspect, embodiments of the present description provide methods for preparing personal care composition. Generally described, the method comprises mixing an acidified pectin with water, preferably demineralized water or deionized water, to provide a mixture of a personal care composition, heating the mixture while mixing to a temperature of about 70° C. to about 90° C. for a time sufficient to dissolve the acidified pectin in the personal care composition, and cooling the personal care composition to a temperature below about 70° C.

Embodiments of the present description are further illustrated by the following examples, which are not to be construed in any way as imparting limitations upon the scope thereof. On the contrary, it is to be clearly understood that resort may be had to various other embodiments, modifications, and equivalents thereof which, after reading the description therein, may suggest themselves to those skilled in the art without departing from the spirit of the present invention and/or the scope of the appended claims. Unless otherwise specified, quantities referred to by percentages (%) are by weight (wt %).

EXAMPLES

Example 1

Pectins were acidified by mixing the pectin (200 g) with a hydrochloric acid-containing iso-propanol mixture (1500 ml 60% iso-propanol containing 75 ml 37% hydrochloric acid). The mixture was stirred at room temperature for 20 minutes, drained through filter paper, and rinsed with 4000 ml 60% iso-propanol to remove excess acid. The pectin was subsequently rinsed with 250 ml 100% iso-propanol, drained on filter paper, dried overnight at 65° C., and sieved.

Pectins that were acidified included (1) amidated low ester pectins with degree of amidation of about 24% obtained from CP Kelco ApS and made according to the methods described in U.S. Pat. No. 2,480,710, and (2) low ester pectins with a degree of esterification of 30%, 38% and 50% obtained from CP Kelco ApS and made according to the methods described in US 2006/1279916 without the amidation step. The intrinsic viscosity of the non-amidated pectins was 5-6 dl/g.

A skin care formulation was prepared by mixing glycerin and demineralized water to prepare a 5% glycerin solution. The pectin was dispersed in the glycerin solution while stirring, and preservatives (0.07% sorbic acid and 0.1% benzoic acid) were added. The dispersion was heated in a water bath to 75-90° C. while stirring and maintained at that temperature for 15-25 minutes until the pectin was dissolved. Net weight was adjusted with the demineralized water, and the formulation was cooled at room temperature overnight. The viscosity was measured on a Brookfield viscometer LVT, spindle 4 at room temperature. Not wishing to be bound by any theory, those of ordinary skill in the art will appreciate that the Brookfield viscometer may form a "hole" in certain gel-like preparations. Thus, the apparent viscosity (i.e., the viscosity that was measured) may be lower than the actual viscosity of the composition.

The amidated low ester pectins were acidified to a pH in the range of 3-4 before preparing the skin care formulations. The properties of the skin care formulations prepared using the acidified amidated low ester pectins are summarized in the table below.

| Conc. % | Pectin pH | Solution pH | Viscosity cP | Gel | Thickness | Smoothness | Flow | Other |
|---|---|---|---|---|---|---|---|---|
| 2.0 | 3.80 | 3.45 | 3200 | Moderate | Very thick | Not Smooth | Flows | Some gel lumps |
| 2.0 | 3.00 | 2.71 | 2360 | Moderate | Very thick | Not smooth | Flows | Gel lumps; Not fully dissolved |
| 1.0 | 3.00 | 2.80 | 230 | Weak | Thin | Smooth | Flows | No gel lumps; |
| 1.5 | 3.00 | 2.86 | 790 | Weak | Rather thin | Smooth | Flows | No gel lumps |

The low ester pectins with a DE of about 30%, about 38%, and about 50% were acidified to a pH in the range of 2.8-3.8. The skin care formulations were then prepared with the acidified low ester pectins at concentrations from 2.5% to 3%, and the viscosity of the formulations was measured and the organoleptic properties were characterized. The properties of the skin care formulations prepared using the acidified low ester pectins are summarized in the table below.

| DE | Conc. % | Pectin pH | Solution pH | Viscosity cP | Evaluation |
|---|---|---|---|---|---|
| 30 | 2.5 | 3.6 | 3.65 | 30,600 | Slightly gelled; Flowable; Easy to spread; Non-tacky; Absorbs fast; Non-astringent |
| 30 | 2.5 | 3.4 | 3.42 | 38,800 | Slightly gelled; Flowable; Easy to spread; Non-tacky; Absorbs fast; Non-astringent |
| 30 | 3 | 3.8 | 3.76 | 26,500 | No gel; Rather thin; Non-tacky; Absorbs fast; Non-astringent |
| 30 | 3 | 3.6 | 3.56 | 326,400 | Gelled; Very thick; Tacky; Absorbs slowly; Non-astringent |

-continued

| DE | Pectin Conc. % | Pectin pH | Solution pH | Viscosity cP | Evaluation |
|----|----|----|----|----|----|
| 30 | 3 | 3.4 | 3.26 | 369,600 | Gelled; Very thick; Tacky; Absorbs slowly; Non-astringent |
| 30 | 3 | 3.0 | 2.91 | 79,000 | Gelled; Flowable; Slightly tacky; Absorbs slowly; Non-astringent |
| 30 | 3 | 2.8 | 2.7 | 39,950 | Slightly gelled; Flowable; Easy to spread; Tacky; Absorbs slowly; Film on skin; Non-astringent |
| 38 | 3 | 3.8 | 3.70 | 8,190 | No gel; Thin; Slightly tacky; Absorbs fast |
| 38 | 3 | 3.6 | 3.58 | 29,000 | Slightly gelled; Flowable; Easy to spread; Slightly tacky; Absorbs fast; Non-astringent |
| 38 | 3 | 3.4 | 3.29 | 39,300 | Slightly gelled; Flowable; Easy to spread; Slightly tacky; Absorbs fast; Non-astringent |
| 38 | 3 | 3.0 | 2.86 | 29,950 | Slightly gelled; Flowable; Easy to spread; Slightly tacky; Absorbs fast; Non-astringent |
| 38 | 3 | 2.8 | 2.71 | 30,050 | No gel; Somewhat thin; Easy to spread; Slightly tacky; Absorbs fast; Non-astringent |
| 38 | 3 | 2.6 | 2.55 | 24,600 | No gel; Somewhat thin; Easy to spread; Slightly tacky; Absorbs fast; Non-astringent |
| 38 | 3.5 | 3.0 | 2.95 | 43,300 | Slightly gelled; Flowable; Easy to spread; Non-tacky; Absorbs fast; Non-astringent |
| 38 | 4 | 3 | 2.96 | 386,400 | Slightly gelled; Flowable; Easy to spread; Slightly tacky; Absorbs fast; Non-astringent |
| 50 | 4.0 | 2.8 | 2.74 | 41,600 | No gel; Tacky; Absorbs slowly; Non-astringent |
| 50 | 4.0 | 3 | 2.98 | 49,000 | No gel; Tacky; Absorbs slowly; Non-astringent |
| 50 | 4.0 | 3.2 | 3.18 | 47,850 | No gel; Tacky; Absorbs slowly; Non-astringent |
| 50 | 4.0 | 3.4 | 3.43 | 26,200 | No gel; Thin; Tacky; Absorbs slowly; Non-astringent |
| 50 | 4.0 | 3.6 | 3.54 | 10,000 | No gel; Very thin; Tacky; Absorbs slowly; Non-astringent |

As can be seen from the foregoing, the acidified amidated low ester pectins did not provide the texture desired for the skin care formulations. In the tested pH range, the preparations either became pre-gelled or too thin, which may have been caused by the difficulty in dissolving the amidated pectin.

The acidified non-amidated low ester pectins, however, provided skin care formulations having the desired texture. For example, the acidified low ester pectin with a DE of about 30% provided a formulation with a gelled texture, non-tacky to tacky feel on the skin, and was non-astringent with a pH range of 3.7-2.9. Pectin concentrations were in the range 2-4%, however, particularly desirable properties were obtained for pectin concentrations of 2.5% and having a pH of 3.4-3.6. The resulting formulations had a viscosity in the range of about 75,000 cP to about 400,000 cP.

The acidified low ester pectin with a DE of about 38% also provided a formulation with a slightly gelled texture and which was slightly tacky or non-tacky with a pH in the range 2.8-3.6. Pectin concentrations ranging from 3-4% provided formulations having viscosities in the range of 30,000 cP to about 40,000 cP.

The acidified low ester pectin with a DE of about 50%, however, provided formulations that were characterized as lacking the desired gel-like texture and were too thin, too tacky and took too long for absorption on the skin.

Example 2

The acidified low ester pectins prepared in Example 1 were subsequently tested to determine the effect of prolonged temperature exposure on the properties of the formulations. The formulations were prepared by mixing 5% glycerin and 4% of the acidified low ester pectin (DE of 38%, 2.4-3.7 pH) in demineralized water and heating the mixture to 90° C. while stirring. The formulation was then stored at 90° C., or cooled and stored at 70° C., and samples were taken at after 30 minutes, 1 hour, 3 hours, 4 hours and 4.5 hours to determine the effect of prolonged temperature exposure. The viscosity was then measured at 25° C.

| Temperature ° C. | Storage time min | Viscosity cP | Comment |
|----|----|----|----|
| 90 | 30 | 160800 | Very thick |
| 90 | 60 | 45800 | Very thick |
| 90 | 180 | 588 | Thin |
| 90 | 240 | 204 | Thin |
| 90 | 270 | 31 | Very thin |
| 70 | 30 | 176600 | Very thick |
| 70 | 60 | 152800 | Very thick |
| 70 | 150 | 128600 | Very thick |
| 70 | 240 | 97000 | Very thick |
| 70 | 270 | 98000 | Very thick |

The viscosity of the formulation exposed to a temperature of 90° C. dropped substantially within the first hour. This effect also was observed organoleptically, with the formulation clearly becoming noticeably thinner. The viscosity of the formulation exposed to a temperature of 70° C. had a slower viscosity drop, however, and organoleptically showed no substantial reduction of the thickness of the formulation. Thus, skin care formulations including the acidified pectins should be reduced from temperatures greater than 70° C. to below 70° C. as quickly as possible.

Example 3

A low ester pectin having a pH of 4.8 was acidified to obtain an acidified low ester pectin having a pH of 3.32. A 3% solution of each pectin in demineralized water (6.75 pH) was prepared. Each solution was used to treat the skin of a 61 year old male volunteer over a 24 hour period using the following protocol, the first day without using either pectin solution, the second day using the acidified low ester pectin solution (3.32 pH), and the third day using the non-acidified low ester pectin solution (4.8 pH).

a. Evening:
  i. Skin pH was measured in the evening using a pH meter (Skincheck, Hanna Instruments, model 14198110);
  ii. Hands were then thoroughly washed with Sara Lee® Neutral hand soap (pH=9.38) and the skin-pH was measured;
  iii. Back of the hand was treated with 0.3-0.4 g of the pectin solution and the skin-pH was measured;
b. Late Evening:
  i. Skin pH was measured;
c. Morning Before Bathing:
  i. Skin pH was measured;
d. Morning After Bathing:
  i. Skin pH was measured;
  ii. Back of the hand was treated with 0.3-0.4 g of the pectin solution and the skin pH was measured intermittently;
e. Mid-Day:
  i. Skin pH was measured intermittently throughout the day, the hands were subsequently washed thoroughly with soap, and the skin pH was measured again;
  ii. Back of hand was treated with 0.3-0.4 g of the pectin solution and the skin pH was measured.

The results of the foregoing comparison are summarized in the tables below and are illustrated in FIG. 1.

| Comment | | Minutes Elapsed | Activity | Skin-pH |
|---|---|---|---|---|
| Day 1 | No after treatment with pectin | 0 | Before hand washing | 5.65 |
| | | 2 | After hand washing | 6.75 |
| | | 0 | Before bath | 5.56 |
| | | 15 | After bath | 7.35 |
| | | 45 | Before departure | 7.00 |
| | | 105 | After arrival at work | 6.54 |
| | | 165 | At work | 6.12 |
| | | 210 | Before hand washing | 5.93 |
| | | 271 | After hand washing | 7.17 |
| | | 330 | At work | 6.23 |
| | | 435 | Before hand washing | 5.73 |
| | | 436 | After hand washing | 6.98 |
| | | 540 | At work | 6.19 |
| | | 615 | Before hand washing | 5.73 |
| | | 616 | After hand washing | 7.09 |
| | | 1140 | Before bed, no wash | 5.51 |
| Day 2 | After treatment with low ester pectin solution DE = 38 pH = 3.32 Dosage: 0.3-0.4 g | 0 | Before hand washing | 5.90 |
| | | 5 | After hand washing | 7.10 |
| | | 9 | After pectin treatment | 5.57 |
| | | 95 | Before bed no wash | 5.40 |
| | | 0 | Before bath | 5.04 |
| | | 20 | After bath | 7.02 |
| | | 22 | After pectin treatment | 5.55 |
| | | 75 | At work | 5.54 |
| | | 130 | At work | 5.48 |
| | | 195 | Before hand washing | 5.56 |
| | | 197 | After hand washing | 7.15 |
| | | 200 | After pectin treatment | 5.30 |
| | | 250 | At work | 5.43 |
| | | 310 | At work | 5.44 |
| | | 370 | Before hand washing | 5.40 |
| | | 372 | After hand washing | 6.70 |
| | | 374 | After pectin treatment | 5.51 |
| | | 391 | At home | 5.50 |
| | | 456 | At home | 5.41 |
| | | 651 | Before bed no wash | 5.23 |
| Day 3 | After treatment with low ester pectin solution DE = 38 pH = 4.80 Dosage: 0.3-0.4 g | 0 | Before hand wash | 5.85 |
| | | 2 | After hand wash | 7.31 |
| | | 4 | After pectin treatment | 7.21 |
| | | 87 | Before bed | 6.93 |
| | | 0 | Before bath | 5.46 |
| | | 16 | After bath | 7.22 |
| | | 17 | After pectin treatment | 7.17 |
| | | 44 | Departure | 7.07 |
| | | 86 | At work | 7.06 |
| | | 161 | At work | 6.70 |
| | | 221 | At work | 6.23 |
| | | 272 | Before hand wash | 6.20 |
| | | 274 | After hand wash | 6.97 |
| | | 276 | After pectin treatment | 6.89 |
| | | 304 | At work | 6.95 |
| | | 442 | At work | 6.32 |
| | | 477 | Before hand wash | 6.62 |
| | | 479 | After hand wash | 7.39 |
| | | 481 | After pectin treatment | 7.22 |
| | | 567 | At work | 7.22 |
| | | 593 | At home | 6.85 |
| | | 798 | Before bed no wash | 7.15 |

The preparation made with the low pH pectin (pH=3.3) was thick and slightly gelled, whereas the preparation made with the high pH pectin (pH=4.8) was thin and without gelation. As can be seen in FIG. 1, the skin pH peaked after each hand-washing. On Day 1, without subsequent pectin treatment, the skin pH increased to about 7-7.5 and took several hours to return to a level of about 5.5-6. On Day 2, with subsequent treatment with a low pH pectin (pH=3.3), the skin pH immediately dropped to a level of about 5-5.5 and was maintained at this level until after a subsequent washing. However, on Day 3, when treating the skin with a high pH pectin (pH=4.8) after the washing, the skin pH was decreased even more slowly than Day 1 (without any pectin treatment).

Without being bound of theory, it is believed that the high pH pectin acted as a buffer against acid, neutralizing the acid formed by the skin. Conversely, the low pH pectin (pH=3.3) acted as a buffer against alkali, neutralizing the alkalinity of the soap and immediately reducing the skin pH to the desirable levels (i.e., to the optimum pH for the skin barrier promoting enzyme Beta-glucocerebrosidase).

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

What is claimed is:

1. A method for preparing a personal care composition comprising:
   mixing an acidified pectin with water to provide a mixture, wherein the acidified pectin is extracted from a pectin-containing material and has a degree of esterification from about 30 to about 50 and a pH from about 2 to about 4;
   heating the mixture to a temperature from about 70° C. to about 90° C. for a time sufficient to dissolve the acidified pectin in the mixture; and cooling the mixture to a temperature below about 70° C. to provide a personal care composition characterized as a viscous, fluid gel.

2. The method of claim 1, wherein the acidified pectin is prepared by a method comprising:
   providing a low ester pectin extracted from a pectin-containing material having a degree of esterification of about 30 to about 50 and a pH of about 4 to about 5;
   mixing the low ester pectin with a solution of an acid and alcohol for a time sufficient to obtain an acidified pectin having a pH of about 2 to about 4; and
   washing the acidified pectin with alcohol; and
   drying the acidified pectin.

3. The method of claim 1, wherein the personal care composition has a viscosity from about 30,000 to about 400,000 cP.

4. The method of claim 1, wherein the acidified pectin has a pH of about 2.5 to about 3.7.

5. The method of claim 1, wherein the acidified pectin has a degree of esterification from about 30 to about 35 and a pH from about 2.9 to about 3.7, and is present in the personal care composition in an amount from about 2% to about 4% by weight of the personal care composition.

6. The method of claim 5, wherein the acidified pectin has a pH from about 3.4 to about 3.6.

7. The method of claim 5, wherein the personal care composition has a viscosity from about 75,000 to about 400,000 cP.

8. The method of claim 1, wherein the acidified pectin has a degree of esterification from about 36 to about 40 and a pH from about 2.8 to about 3.6, and is present in the personal care composition in an amount from about 3% to about 4% by weight.

9. The method of claim 8, wherein the personal care composition has a viscosity of about 30,000 to about 40,000 cP.

10. The method of claim 1, further comprising adding one or more personal care agents to the personal care composition, the one or more personal care agents being selected from the group consisting of vitamins, peptides, oil control agents, tanning agents, anti-acne agents, desquamation agents, flavonoids, protease inhibitors, non-vitamin antioxidants and radial scavengers, anti-inflammatory agents, antimicrobials, and mixtures thereof.

11. The method of claim 1, wherein the personal care composition is substantially free of low molecular weight acids.

12. The method of claim 1, wherein the personal care composition is substantially free of emulsifiers.

13. The method of claim 1, wherein the personal care composition is in a form suitable for use on human skin.

14. The method of claim 1, wherein the personal care composition is in a form suitable for use on mammalian skin.

15. The method of claim 13, wherein the personal care composition is in a product selected from the group consisting of skin creams, skin lotions, deodorant products, fragrance products, and soap products.

16. A method for preparing a personal care composition comprising:
   mixing an acidified pectin with water to provide a mixture, wherein the acidified pectin is extracted from a pectin-containing material and has a degree of esterification from about 30 to about 50 and a pH from about 2 to about 4;
   heating the mixture to a temperature from about 70° C. to about 90° C. for a time sufficient to dissolve the acidified pectin in the mixture; and
   cooling the mixture to a temperature below about 70° C. to provide a personal care composition characterized as a viscous, fluid gel consisting essentially of the acidified pectin.

17. The method of claim 16, wherein the acidified pectin has a degree of esterification from about 30 to about 35 and a pH from about 2.9 to about 3.7, and is present in the composition in an amount from about 2% to about 4% by weight.

18. The method of claim 17, wherein the personal care composition has a viscosity from about 75,000 to about 400,000 cP.

19. The method of claim 16, wherein the acidified pectin has a degree of esterification from about 36 to about 40 and a pH from about 2.8 to about 3.6, and is present in the composition in an amount from about 3% to about 4% by weight.

20. The method of claim 19, wherein the personal care composition has a viscosity from about 30,000 to about 40,000 cP.

* * * * *